United States Patent
Vadgama et al.

(10) Patent No.: US 6,387,232 B1
(45) Date of Patent: May 14, 2002

(54) MEMBRANE FOR A SENSOR

(75) Inventors: Pankaj Maganlal Vadgama; Andrew David Maines, both of Manchester (GB)

(73) Assignee: SensAlyse Holdings Limited, Manchester (GB)

( * ) Notice: Subject to any disclaimer, the term of this patent is extended or adjusted under 35 U.S.C. 154(b) by 0 days.

(21) Appl. No.: 09/297,744

(22) PCT Filed: Nov. 7, 1997

(86) PCT No.: PCT/GB97/03005

§ 371 Date: Jul. 16, 1999

§ 102(e) Date: Jul. 16, 1999

(87) PCT Pub. No.: WO98/20333

PCT Pub. Date: May 14, 1998

(30) Foreign Application Priority Data

Nov. 7, 1996 (GB) .............................................. 9623147

(51) Int. Cl.[7] ........................ G02N 27/26; B01D 39/14
(52) U.S. Cl. ................... 204/403; 204/418; 210/500.29
(58) Field of Search ................................ 204/403, 418, 204/415; 210/500.21, 500.27, 500.3, 500.31, 500.32, 500.29; 427/2.1, 2.11

(56) References Cited

U.S. PATENT DOCUMENTS

| | | | | |
|---|---|---|---|---|
| 3,593,855 A | * | 4/1972 | Stana | 210/500.27 |
| 3,655,526 A | * | 4/1972 | Christian | 205/788.5 |
| 4,891,125 A | * | 1/1990 | Schultz | 204/435 |

FOREIGN PATENT DOCUMENTS

| | | |
|---|---|---|
| EP | 302 661 | 2/1989 |
| EP | 653 630 | 5/1995 |
| GB | 1 442 303 | 7/1976 |
| GB | 2 194 843 | 3/1988 |
| GB | 2 209 836 | 5/1989 |
| WO | 94-02585 | 2/1994 |

OTHER PUBLICATIONS

Maines et al: "Diffusion restricting outer membranes for greatly extended linearity measurements with glucose oxidase enzyme electrodes." ANALYTICA CHMICA ACTA, vol. 333m No.3, Nov. 8, 1996, pp. 223–231, XP002057943.

* cited by examiner

Primary Examiner—Jill Warden
Assistant Examiner—Alex Noguerola
(74) Attorney, Agent, or Firm—Pillsbury Winthrop LLP

(57) ABSTRACT

A membrane for use in a sensor having a detection arrangement. The membrane is of a cellulosic material incorporating a hydrophobic agent (e.g. isopropyl myristate) and is permeable by diffusion to an analyte species of interest to be detected directly or indirectly by the detection arrangement.

2 Claims, 1 Drawing Sheet

Direct anodic (+650mV) response to 2.8mM ascorbate.

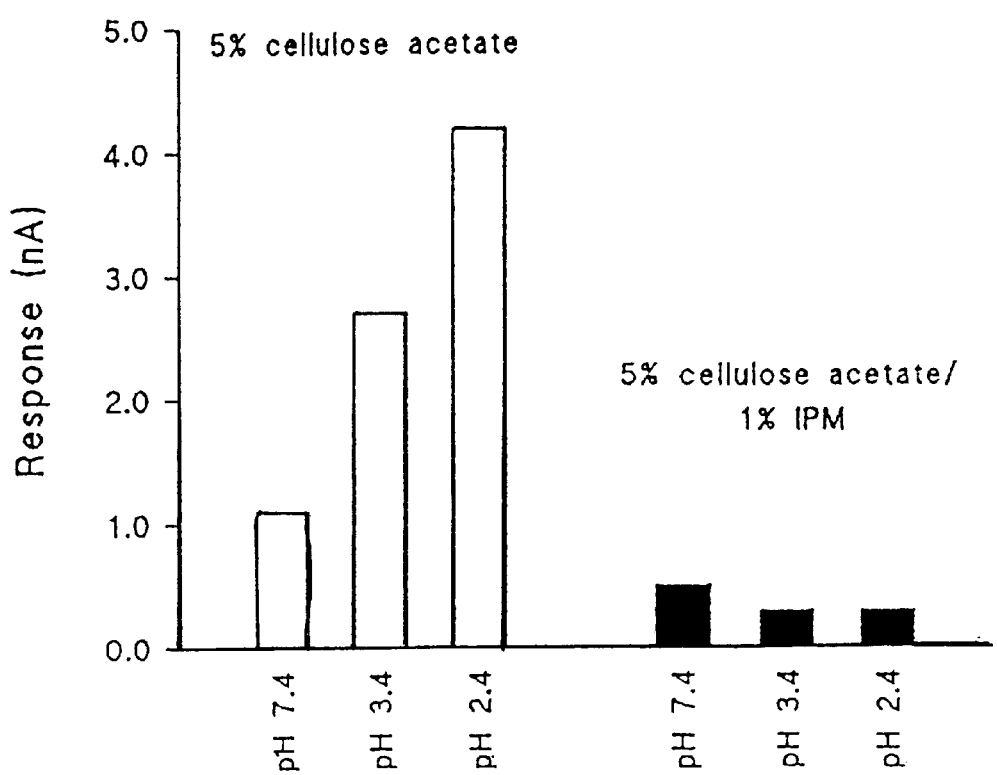

MEMBRANE FOR A SENSOR

The present invention relates to a membrane and to a sensor (particularly but not exclusively a biosensor) incorporating such a membrane.

Various sensors are known which incorporate a membrane permeable by diffusion to an analyte species of interest whereby the species may be directly or indirectly detected by a detection arrangement provided at one side of the membrane. The detection arrangement may be an electrochemical detection arrangement (e.g. an enzyme electrode). Examples of such sensors are biosensors incorporating an enzyme electrode whereof the enzyme is capable of interaction with the selected analyte to produce a change which may be determined by the electrode arrangement as an indirect representation of the presence or amount of the analyte. By way of example, there may be mentioned a glucose biosensor based on the enzyme glucose oxidase which catalyses the oxidation of glucose by molecular oxygen to gluconic acid and hydrogen peroxide. The increased in hydrogen peroxide concentration or decrease in oxygen concentration may be determined by an amperometric electrode.

Such glucose biosensors may be used for the determination of glucose in either blood or fruit juice.

A problem does however exist with sensors based on electrochemical detection systems in the case where the sample being analysed contains ascorbate species in addition to the particular analyte of interest since ascorbate is an interferent in the electrochemical detection. It will thus be appreciated that ascorbate is an interferent in the determination of glucose in fruit juice.

A solution to the problem of ascorbate interferents is to use an ascorbate rejecting membrane between the electrochemical detection system and the sample being analysed. However the known membranes have the disadvantage that they only reject ascorbate over a relatively limited pH range and are not effective at the acidic pH values of fruit juice. Thus for example, unmodified cellulose acetate becomes ineffective around the pKa of ascorbate (pH 4.1) and is only really effective above ca pH6.

It is therefore an object of the present invention to obviate or mitigate the abovementioned disadvantage.

According to a first aspect of the present invention there is provided a membrane for use in a sensor having a detection arrangement said membrane being permeable by diffusion to an analyte species of interest to tie detected directly or indirectly by the detection arrangement wherein said membrane is of a cellulosic material incorporating a hydrophobic agent.

By direct detection we mean that the permeating species is itself detected. By indirect detection we mean that the permeating species after passing through the membrane, interacts with a further component to generate the actual species which is detected.

According to the present invention there is provided a sensor comprising an electrochemical detection arrangement and a membrane in accordance with the first aspect of the invention positioned in use of the sensor between said arrangement and the sample being analysed.

We have found that cellulosic membranes incorporating hydrophobic agents are capable of ascorbate rejection over a wide range of pH values and are therefore useful in the production of sensors which have an electrochemical detection system and which are used in applications where avoidance of ascorbate interference is required. The membranes of the invention have the advantage that they are also wettable, a property which is derived from the Cellulosic nature of the membrane The cellulosic material may, for example, be cellulose, cellulose nitrate or a cellulose ester such as cellulose acetate or cellulose butyrate. Most preferably the membrane is of cellulose acetate. For preference the cellulose acetate has an acetate content of 35% to 45% by weight. e.g. about 40% by weight.

The amount of hydrophobic agent incorporated in the membrane is preferably 1 to 90% by weight (based on the total weight of the membrane). More preferably this amount is 1% to 50%, even more preferably 10% to 50%, and most preferably 14% to 45%. Thus, for example, the membrane may comprise 14% to 30%. more specifically 14% to 20% by weight of the hydrophobic agent.

The hydrophobic agent may, for example, be a substantially water immiscible fatty or oily substance, for example a lipid or ester.

Preferred hydrophobic esters are lower alkyl (e.g $C_1$–$C_1$) esters of long chain aliphatic acids (e.g. having a chain length of up to 18 carbon atoms). A particularly preferred ester is iso-propyl myristate. Other esters which may be used are esters of organic acids, e.g. dioctyl phthalate, as well as esters such as dioctyl adipate. A further hydrophobic agent which may be used is diphenyl ether.

A sensor in accordance with the invention may, for example, be a biosensor comprising an enzyme layer which is capable of interacting with an analyte species of interest to produce an electrochemically detectable change, an electrochemical detection system on one side of the layer for detecting said change, and a membrane in accordance with the first aspect of the invention provided either between the enzyme layer and the detection arrangement or on the side of the enzyme layer remote from the detection arrangement.

The membrane may have a thickness of 0.1 to 200 microns, preferably 4 to 50 microns.

Membranes in accordance with the invention may be produced by conventional casting techniques in which a solution of the cellulosic material and the requisite amount of the ester in a volatile solvent is cast usually onto a flat surface and the solvent allowed to evaporate. Alternatively it is possible to employ a "spin casting" technique in which the membrane is produced by applying a solution (of the type defined in the previous sentence) to a flat surface which is then rotated (usually about a vertical axis) at a speed which causes the solution to be evenly distributed and the solvent to be evaporated so as to produce a membrane of uniform thickness.

The enzyme layer may be provided using conventional techniques, e.g. by immobilising the enzyme in a cross-linked glutaraldehyde matrix. If desired the enzyme layer may be supported on a highly permeable membrane (e.g. a dialysis membrane) or between two such membranes.

The membrane can be used as a diffusion restricting membrane and is therefore advantageously used as the outer membrane combining properties of diffusion restriction and pH independent ascorbate rejection. Furthermore, in the case of glucose sensors, the use of the membrane confers extreme linearity for glucose in addition to the properties outlined in the previous sentence. Since the membrane has diffusion restricting and glucose linearising properties it is possible to use the membrane of the invention in sensors having a detection arrangement other than an electrochemical detection arrangement.

It is also possible for the membrane to be used as an inner membrane of a sensor, i.e. between an enzyme layer and the detection arrangement.

The invention will be described further by reference to the following nonlimiting Example and accompanying drawing which illustrates the results of the Example.

EXAMPLE

Chemicals

Sodium ascorbate, hydrochloric acid. cellulose acetate (39.8% acetyl content), acetone (99.9+% HPLC grade) and isopropyl myristate (IPM) were from Aldrich (Poole, UK). Sodium dihydrogen-phosphate, disodium hydrogen-phosphate, magnesium chloride, sodium hydroxide and aluminium oxide were from BDH (Poole, UK).

Buffer

A buffer comprising 18.4 mmoles $l^{-1}$ $Na_2HPO_4$, 1.0 mmoles $l^{-1}$ $MgCl_2$ was prepared in distilled water and adjusted to pH 7.4. 3.4 or 2.4 with HCl or NaOH. All solutions were made up in this buffer.

Membranes

A cellulose acetate membrane was formed by spin-coating 1 ml of 5% w/v cellulose acetate in acetone solution containing 1% v/v iso-propyl myristate (IPM) onto a 1 $cm^2$ piece of Cuprophan dialysis membrane (Gambro, Lund, Sweden) at 1000 rpm for 60s using a photo-resist spinner (E/C101D-R485, Headway Research Inc., Garland, Tex., USA). This procedure yielded and IPM-modified cellulose acetate coated dialysis membrane. The cellulose acetate membrane contained 14.5% by weight (based on the total weight of the cellulose acetate membrane) of IPM. An unmodified membrane was prepared using the same procedure but omitting the IPM from cellulose acetate solution.

Apparatus and Electrode Assembly

The membranes prepared as described above were tested for ascorbate rejection properties using an amperometric cell (Rank Brothers, Bottisham, UK) which consisted of a central 2 mm diameter platinum working electrode with an outer concentric 12 mm diameter and 1 mm wide silver ring (Ag/AgCl) as a counter/ reference electrode. Before use, the electrodes were polished with wet and then dry aluminium oxide powder. The electrodes were then covered with a small volume of pH 7.4 buffer and the unmodified or IPM-modified cellulose acetate-coated dialysis membrane was placed over the electrodes with the coating uppermost. The working electrode was polarised at +650 mV (vs. Ag/AgCl) for the oxidation of enzymatically generated $H_2O_2$, using a potentiostat (Chemistry Workshops, University of Newcastle, UK) with an output to chart recorder (Lloyd Instruments. Fareham, UK) for recording of the current/time response.

Baseline current in buffer (<5 nA) was attained before measurement. 1 ml of 2.8 mmoles $l^{-1}$ of buffered (pH 7.4. 3.4 or 2.4) ascorbate solution was then added to the sample chamber and the current/time response was monitored. Between successive exposures the sample chamber was rinsed three times with buffer and left to recondition for 30 min. As indicated, measurements were made with the modified and unmodified membranes. The results are shown in the accompanying drawing.

It will be seen from the drawing that the IMP-modified membrane had significant ascorbate rejection properties at all pH values tested, i.e. 7.4. 3.4 and 2.4. The results are to be contrasted with those for the unmodified membrane from which it will be seen that, at all pH values, the IMP modified membrane gave results superior to the best result (at pH 7.4) for the unmodified membrane.

Membranes have also been produced from 1 ml of 5% w/v cellulose acetate in acetone solution containing 2% to 5% v/v IPM and have been tested for exclusion of ascorbate at pH 3.4. The percentage reduction (at pH 3.4) in 2.8 mM ascorbate response compared with a membrane formed from a 5% solution of unmodified cellulose acetate were found to be

5% CA/1% IPM=89%
5% CA/2% IPM=91%
5% CA/5% IPM=99%

Ascorbate rejection actually improves with increasing IPM content but this is compromised by a reduction in analyte (glucose) flux. Therefore there is a trade off between ascorbate rejection and sensitivity to the analyte, and 5% CA/1% IPM is the right "balance" for most applications.

What is claimed is:

1. A membrane for use in a sensor having a detection arrangement, said membrane being permeable by diffusion to an analyte species of interest to be detected directly or indirectly by the detection arrangement wherein said membrane is a solvent cast membrane obtained by casting a solution of a cellulosic material incorporating a hydrophobic agent and evaporating the solvent, and wherein the hydrophobic agent is isopropyl myristate.

2. A biosensor comprising an enzyme layer which is capable of interacting with an analyte species of interest to produce an electrochemically detectable change, an electrochemical detection system on one side of the layer for detecting said change, and a membrane being permeable by diffusion to the analyte species of interest to be detected directly or indirectly by the electrochemical detection system, wherein said membrane is a solvent cast membrane obtained by casting a solution of a cellulosic material incorporating a hydrophobic agent and evaporating the solvent, said membrane provided either between the enzyme layer and the electrochemical detection system or on the side of the enzyme layer remote from the electrochemical detection system.

* * * * *